(12) United States Patent　　　(10) Patent No.: US 8,998,948 B2
Hyodo　　　(45) Date of Patent: Apr. 7, 2015

(54) MANIPULATOR

(75) Inventor: Ryoji Hyodo, Tokyo (JP)

(73) Assignee: Olympus Corporation, Tokyo (JP)

( * ) Notice: Subject to any disclaimer, the term of this patent is extended or adjusted under 35 U.S.C. 154(b) by 406 days.

(21) Appl. No.: 13/069,859

(22) Filed: Mar. 23, 2011

(65) Prior Publication Data

US 2011/0288579 A1　Nov. 24, 2011

(30) Foreign Application Priority Data

May 18, 2010　(JP) ................ P2010-114164

(51) Int. Cl.
| A61B 17/00 | (2006.01) |
| A61B 17/29 | (2006.01) |
| A61B 17/28 | (2006.01) |
| A61B 17/44 | (2006.01) |
| A61B 19/00 | (2006.01) |

(52) U.S. Cl.
CPC ............. *A61B 17/29* (2013.01); *A61B 17/2804* (2013.01); *A61B 17/282* (2013.01); *A61B 2017/2937* (2013.01); *A61B 2017/2939* (2013.01); *A61B 2017/447* (2013.01); *A61B 2019/301* (2013.01)

(58) Field of Classification Search
CPC ............. A61B 2017/2937; A61B 2017/2939; A61B 17/447; A61B 17/282; A61B 17/2812; A61B 17/28; A61B 17/2833; A61B 2017/2808; A61B 2017/2825; A61B 2017/2626; A61B 2017/2932
USPC .................................. 606/205–209
See application file for complete search history.

(56) References Cited

U.S. PATENT DOCUMENTS

| 7,373,219 | B2 * | 5/2008 | Nowlin et al. ................ 700/245 |
| 2004/0193213 | A1 * | 9/2004 | Aranyi et al. ................ 606/205 |
| 2005/0059985 | A1 * | 3/2005 | Kimura ........................ 606/151 |

FOREIGN PATENT DOCUMENTS

| JP | 06030946 A | * | 2/1994 |
| JP | H06-030946 |   | 2/1994 |
| JP | 11-113918 A |   | 4/1999 |
| JP | 2004-129871 A |   | 4/2004 |

OTHER PUBLICATIONS

Japanese Office Action dated Dec. 3, 2013 in counterpart Japanese Patent Application No. 2010-114164.

* cited by examiner

*Primary Examiner* — Katherine Dowe
*Assistant Examiner* — Kendra Obu
(74) *Attorney, Agent, or Firm* — Scully, Scott, Murphy & Presser, PC

(57) ABSTRACT

Provided is a manipulator including a first forceps piece and a second forceps piece, which are connected by a pivotal axle and have a gripping part opened or closed on a leading end side thereof. The manipulator includes a manipulation member that is connected to a base end side of the pair of forceps pieces, and moves forward or backward in an axial direction to open or close the gripping part, a first buffer part that has a first spring constant, and undergoes elastic deformation to change a grasping force generated at the gripping part on the basis of the first spring constant and a pulling amount of the manipulation member, and a stopper that regulates the elastic deformation of the first buffer part.

5 Claims, 6 Drawing Sheets

MANIPULATOR

BACKGROUND OF THE INVENTION

1. Field of the Invention

The present invention relates to a manipulator, and more particularly, to a manipulator having a gripping part grasping an object.

This application claims priority to and the benefits of Japanese Patent Application No. 2010-114164 filed on May 18, 2010, the disclosure of which is incorporated herein by reference.

2. Background Art

In the medical field, manipulators have been used to grasp biological tissue, surgical instruments or the like to conduct procedures.

As one of the manipulators, grip forceps having a forceps part that is freely closed or opened are disclosed in Japanese Unexamined Patent Application Publication No. H06-030946. A manipulation axle is connected to the forceps part via a link mechanism. The forceps part is closed or opened by pulling or pushing the manipulation axle.

The forceps part of the grip forceps disclosed in Japanese Unexamined Patent Application Publication No. H06-030946 is provided with a gripping part having means displaced or deformed by a weaker force than a force that destroys biological tissue or a surgical instrument. Thus, even when a user pulls the manipulation axle with a strong force when grasping the biological tissue or the like, the gripping part is deformed or displaced, thereby preventing damage to the biological tissue or breakage of the surgical instrument.

SUMMARY OF THE INVENTION

In the procedure using a manipulator, an optimal value of a gripping force applied to an object via a gripping part varies depending on conditions under which the gripping part is used. That is, when biological tissue is grasped without damage, a relatively small grasping force is optimal. On the other hand, when a surgical instrument such as a curved needle is grasped, a greater grasping force is suitable so as to prevent the surgical instrument from being dropped. However, it does not necessarily preferable to increase the grasping force. If the grasping force cannot be adjusted, the surgical instrument is deformed, or is easily separated from the gripping part.

Thus, the fact that the manipulator can grasp the object with a constant grasping force does not mean that the manipulator has sufficient manipulability.

In the manipulator disclosed in Japanese Unexamined Patent Application Publication No. H06-030946, the grasping force suitable to grasp the biological tissue is obtained. However, since this manipulator grasps the surgical instrument with the same grasping force, it does not cause damage to the biological tissue, but it cannot firmly grasp the surgical instrument.

For this reason, whenever the object to be grasped is changed from the biological tissue to the surgical instrument, it is necessary to exchange the manipulator.

In this manner, if the manipulator can grasp the object with a weak grasping force, but not secure a greater and adjustable grasping force, it does not follow that the manipulator has sufficient manipulability.

A manipulator of the present invention includes a pair of forceps pieces which are connected by a pivotal axle and have a gripping part opened or closed on a leading end side thereof; a manipulation member that is connected to a base end side of the pair of forceps pieces and moves forward or backward in an axial direction to open or close the gripping part; a buffer part that has a first spring constant and undergoes elastic deformation to change a grasping force acting on an object from the gripping part on the basis of the first spring constant and a pulling amount of the manipulation member; and a stopper that regulates the elastic deformation of the buffer part.

The manipulator of the present invention may further includes a second buffer part, which has a second spring constant greater than the first spring constant and undergoes elastic deformation after at least the stopper regulates the elastic deformation of the buffer part to change the grasping force on the basis of the second spring constant and the pulling amount of the manipulation member.

Further, the stopper may be configured to allow changing a timing when the elastic deformation of the buffer part is regulated.

Another manipulator of the present invention includes a pair of forceps pieces which are connected by a pivotal axle and have a gripping part opened or closed on a leading end side thereof; a manipulation member that is connected to a base end side of the pair of forceps pieces and moves forward or backward in an axial direction to open or close the gripping part; a first buffer part and a second buffer part that have a first spring constant and a second spring constant respectively, and undergo elastic deformation to change a grasping force acting on an object from the gripping part on the basis of a resultant spring constant that is a sum of the first spring constant and the second spring constant and a pulling amount of the manipulation member.

One of the first buffer part and the second buffer part, which has a smaller spring constant than the other, may be fully compressed with a smaller pulling amount of the manipulation member.

Further, the expression "fully compressed" used here refers to a state where a buffer part (a spring, rubber, or the like) is compressed by a load, and is hardly subjected to elastic deformation.

Another manipulator of the present invention includes a pair of forceps pieces which are connected by a pivotal axle and have a gripping part opened or closed on a leading end side thereof; a manipulation member that is connected to a base end side of the pair of forceps pieces and changes a pulling amount to adjust a grasping force acting on an object from the gripping part; a buffer part that generates the grasping force acting on the object from the gripping part on the basis of a first constant and the pulling amount when the pulling amount falls within a first range, and generates the grasping force acting on the object from the gripping part on the basis of a second constant and the pulling amount when the pulling amount falls within a second range having a greater absolute value than the first range.

In the manipulator, when the pulling amount falls within a range having a greater absolute value than the second range, the grasping force acting on the object from the gripping part on the basis of a constant different from the first constant and the second constant and of the pulling amount may be generated.

BEST MODE FOR CARRYING OUT THE INVENTION

Figure 1:
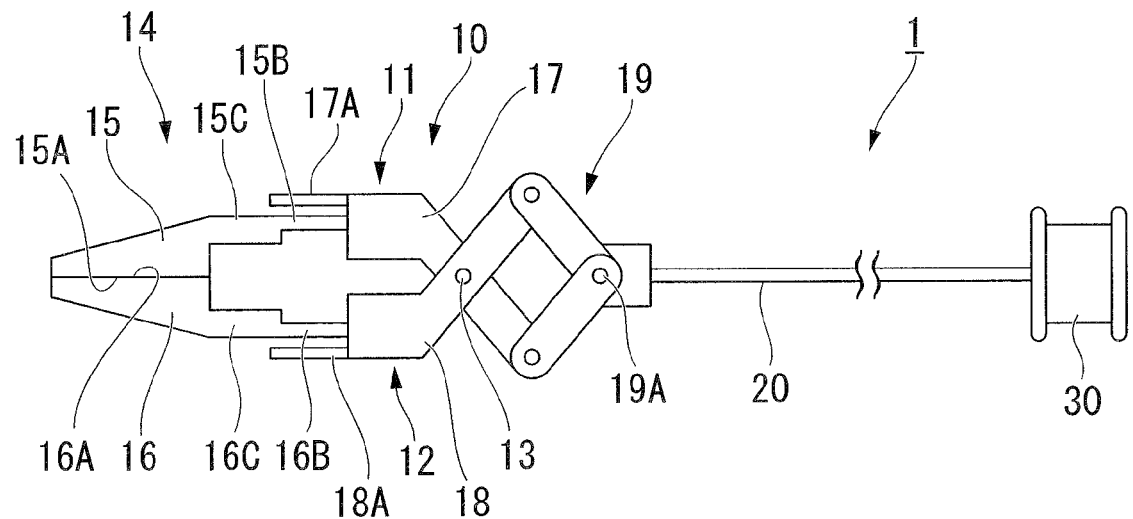
FIG. 1 shows a configuration of main parts of a manipulator according to a first embodiment of the present invention.

A first embodiment of the present invention will be described with reference to FIGS. 1 to 4. FIG. 1 shows a configuration of main parts of a manipulator 1 according to the embodiment. The manipulator 1 is a medical manipulator, and includes a treatment part 10 performing a variety of treatments, a manipulation member 20 manipulating the treatment part 10, and a slider 30 connected to the manipulation member 20.

Further, in the following description, a side where the treatment part 10 is provided is defined as a leading end side, and a side where the slider 30 is provided is defined as a base end side.

The treatment part 10 includes a pair of forceps pieces made up of a first forceps piece 11 and a second forceps piece 12. The first forceps piece 11 and the second forceps piece 12 are coupled to a pivotal axle 13 so as to be pivotable in relation to each other, and a gripping part 14 is formed on a region of the leading end side beyond the pivotal axle 13. The gripping part 14 is opened and closed to grasp an object such as tissue in a body or a surgical instrument.

The forceps pieces 11 and 12 are provided with respective gripping members 15 and 16 on the leading end side, and respective main bodies 17 and 18 on the base end side. The gripping members 15 and 16 are connected to leading ends of the main bodies 17 and 18, respectively, such that gripping faces 15A and 16A coming into contact with the object are opposite to each other.

The gripping members 15 and 16 connected to the leading ends of the main bodies 17 and 18 are provided with first buffer parts 15B and 16B having a platy shape on the base end sides thereof, respectively. Second buffer parts 15C and 16C having a planar shape are provided between the gripping faces 15A and 16A and the first buffer parts 15B and 16B, respectively.

The first buffer parts 15B and 16B and the second buffer parts 15C and 16C function as leaf springs, and can be elastically deformed in an opening/closing direction (i.e. a direction parallel to a pivotal plane of the pair of forceps pieces) when the gripping part 14 grasps the object. As shown in FIG. 1, in terms of the opening/closing direction, the second buffer parts 15C and 16C are thicker than the first buffer parts 15B and 16B, and thus spring constants of the second buffer parts 15C and 16C (second spring constants) are greater than those of the first buffer parts 15B and 16B (first spring constants).

The main bodies 17 and 18 are provided with stoppers 17A and 18A which extend toward the leading end side. The stoppers 17A and 18A are formed of a rigid material having no flexibility, and leading ends thereof are set at positions which come into contact with the second buffer parts 15C and 16C when the first buffer parts 15B and 16B are subjected to a constant amount of elastic deformation. The stoppers 17A and 18A are configured so that lengths thereof can be adjusted, and thus the positions where the leading ends of the stoppers 17A and 18A come into contact with the second buffer parts 15C and 16C can be adjusted.

A link mechanism 19 is connected with the base end sides of the main bodies 17 and 18. The link mechanism 19 has a known structure, and can open or close the gripping part 14 by displacing a joint 19A toward or away from the pivotal axle 13.

The manipulation member 20 is a line-shaped or rod-shaped member, and is connected to the joint 19A of the link mechanism 19 on the leading end side thereof. The manipulation member 20 is inserted through a tubular member (not shown) such as a sheath or the like so as to be able to move forward or backward in its axial direction. The pivotal axle 13 of the treatment part 10 is fixed so as not to move relative to the tubular member. By causing the manipulation member 20 to move forward or backward in its axial direction, the joint 19A moves toward or away from the pivotal axle 13, so that the gripping part 14 is opened or closed. That is, the manipulation member 20 moves forward or backward in its axial direction, so that a pulling amount of the manipulation member varies. An opening or closing amount of the gripping part 14 varies depending on the pulling amount, so that, when the gripping part 14 grasps the object, the magnitude of a grasping force acting on the object from the gripping part 14 is adjusted.

A material of the manipulation member 20 is not substantially restricted as long as it can appropriately transfer a manipulation input to the treatment part 10 without undergoing excessive expansion or contraction in its axial direction. For example, in the case of a manipulator in which the aforementioned tubular member has flexibility, i.e. a flexible manipulator, a wire formed of metal may be used. Meanwhile, in the case of a manipulator in which the aforementioned tubular member does not have flexibility, i.e. a rigid manipulator, a rod formed of metal may be used.

The slider 30 is mounted on the base end side of the manipulation member 20. The slider 30 is slidably mounted on a main body of the manipulation member (not shown) to which a base end of the tubular member is fixed. When a manipulation input sliding the slider 30 relative to the main body of the manipulation member is performed, the manipulation member 20 moves forward or backward in its axial direction, and thus the pulling amount of the manipulation member 20 varies.

A shape of the slider 30 is not substantially restricted, and it may be properly selected from a variety of known shapes. For example, the slider 30 may have a hole for inserting a finger.

Operation of the manipulator 1 configured as described above when in use will be described.

First, prior to inserting the manipulator 1 into a human body, a user adjusts the lengths of the stoppers 17A and 18A such that the leading ends of the stoppers 17A and 18A come into contact with desired positions of the second buffer parts 15C and 16C.

An object is positioned between the gripping face 15A and the gripping face 16A, and the user slides the slider 30 to the base end side. Thereby, the manipulation member 20 is pulled and move backward to the base end side. As a result, the joint 19A of the link mechanism 19 moves away from the pivotal axle 13, and the first forceps piece 11 and the second forceps piece 12 pivot about the pivotal axle 13, so that the gripping part 14 is closed. At this time, a grasping force with which the object is grasped is generated.

Figure 2:
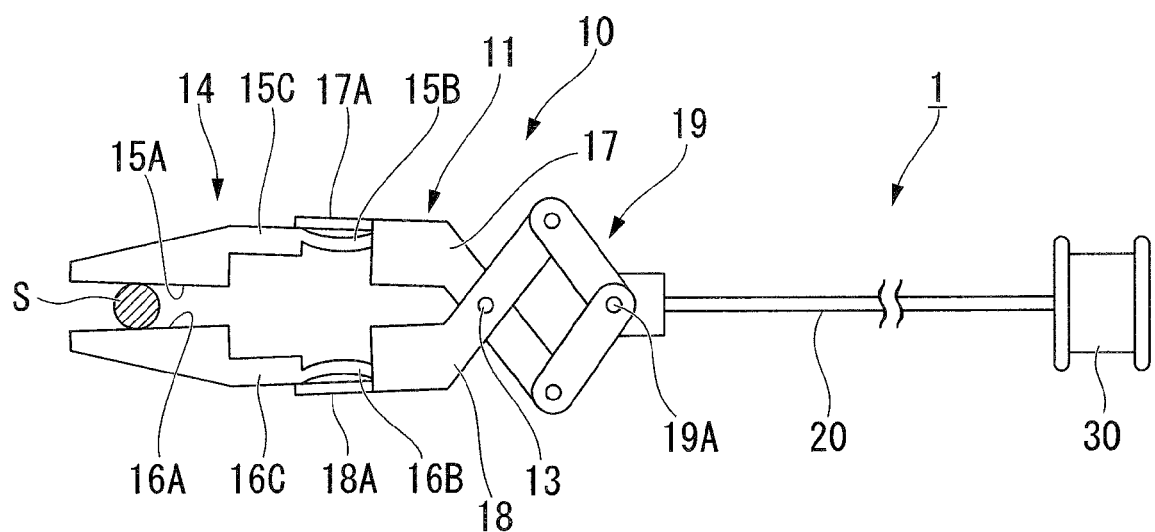
FIG. 2 shows operation when the manipulator is in use.

As shown in FIG. 2, when the gripping part 14 grasps an object S, and thus the gripping faces 15A and 16A come into contact with the object S, the gripping members 15 and 16 are given a reaction force corresponding to rigidity of the object S. Since the spring constants of the second buffer parts 15C and 16C (second spring constants) are greater than those of the first buffer parts 15B and 16B (first spring constants), the first buffer parts 15B and 16B are mainly subjected to elastic deformation first. While the first buffer parts 15B and 16B are mainly subjected to elastic deformation, the grasping force acting on the object S from the gripping part 14 varies on the basis of the first spring constants and the pulling amount of the manipulation member 20 in large part.

Further, in FIG. 2, a case where both of the first buffer parts 15B and 16B are similarly deformed is shown by way of example. However, detailed aspects of the elastic deformation of the first buffer parts 15B and 16B are dependent on various conditions. Both may not be subjected to the same elastic deformation.

When an amount of the elastic deformation of the first buffer parts reaches a predetermined value, that is, when the pulling amount of the manipulation member 20 reaches a predetermined value, the leading ends of the stoppers 17A and 18A come into contact with the second buffer parts 15C and 16C. Thus, the elastic deformation of the first buffer parts is regulated, so that the first buffer parts are prevented from undergoing plastic deformation, and a buffering action of the first buffer parts described above is cancelled.

Figure 3:
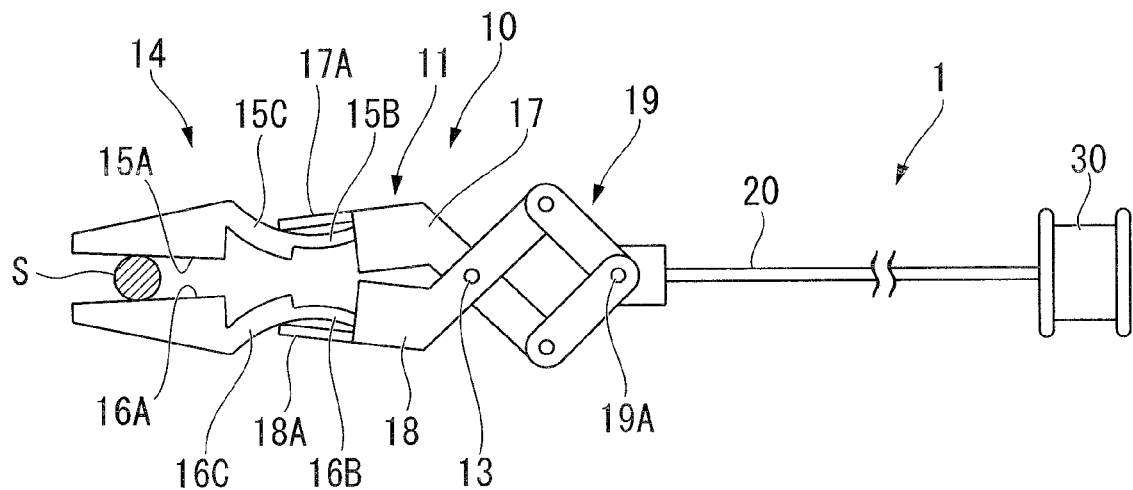
FIG. 3 shows operation when the manipulator is in use.

Further, when the slider 30 slides to the base end side, and thus the pulling amount of the manipulation member 20 increases, the second buffer parts 15C and 16C undergo elastic deformation, as shown in FIG. 3. The grasping force acting on the object S from the gripping part 14 varies on the basis of the second spring constants and the pulling amount of the manipulation member 20.

Figure 4:
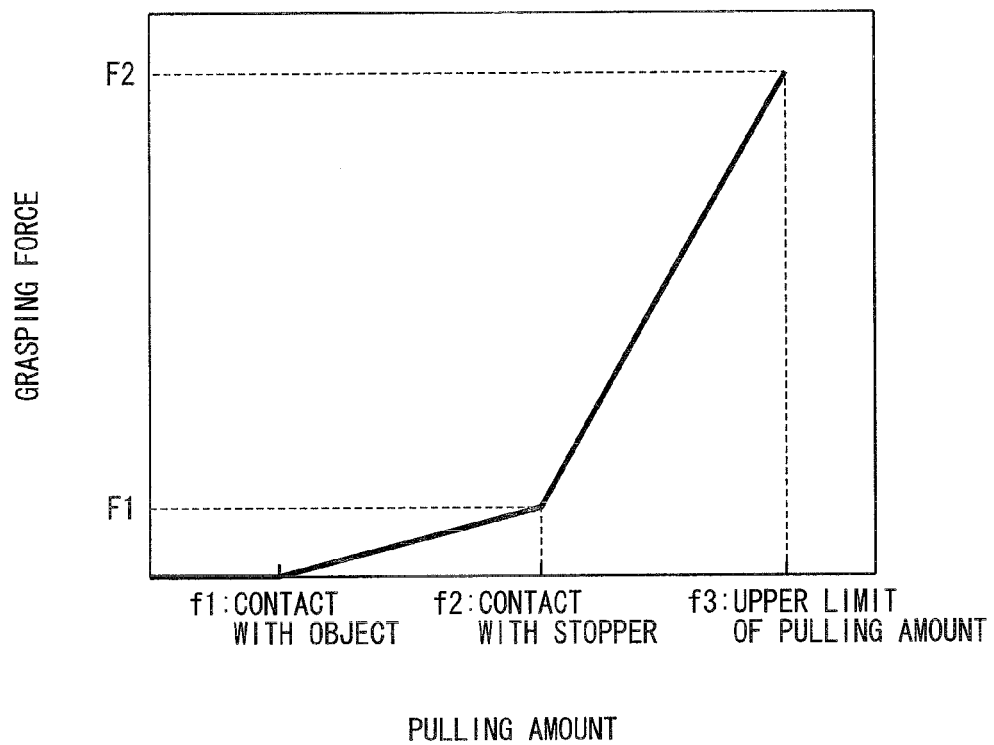
FIG. 4 is a graph schematically showing a relationship between a pulling amount of a manipulation member and a grasping force in the manipulator

FIG. 4 is a graph schematically showing a relationship between the pulling amount of the manipulation member 20 and the grasping force in the manipulator 1. When the manipulation member 20 is pulled by manipulation of the slider 30, the gripping faces 15A and 16A come into contact with the object S. In this case, the pulling amount of the manipulation member 20 is defined as f1. If the pulling amount is greater than f1, the elastic deformation of the first buffer parts is initiated mainly, and the grasping force increases mainly based on the first spring constants and the pulling amount of the manipulation member 20. When the pulling amount increases to reach f2, the buffering action of the first buffer parts is cancelled due to the stoppers. At this time, the grasping force is F1. Afterwards, only the second buffer parts are elastically deformed. The grasping force increases on the basis of the second spring constants and the pulling amount of the manipulation member 20. The pulling amount of the manipulation member 20 can increase up to an upper limit caused by restriction of the slider 30 or the like. Here, f3 is set to the upper limit of the pulling amount. When the pulling amount is f3, the grasping force reaches a maximum value F2. In the present embodiment, since the second spring constants have a greater value than the first spring constants, a slope of the grasping force increases between f2 and f3 is greater than a slope of the grasping force increases between f1 and f2.

In this manner, in the manipulator 1, when the pulling amount falls within a range from f1 to f2 (a first range), the grasping force increases mainly based on the first spring constants and the pulling amount of the manipulation member 20. The first spring constants are set so that a grasping force with which it is easy to grasp a first object (e.g. biological tissue) is obtained within the first range. When the pulling amount falls within a range which is greater than f2 and is equal to or smaller than f3 (a second range), the grasping force increases on the basis of the second spring constants and the pulling amount of the manipulation member 20. The second spring constants are set so that a grasping force which has a proper value in order to grasp a second object (e.g. a surgical instrument such as a curved needle) is obtained within the second range. Within the second range, the pulling amount is adjusted, thereby allowing the grasping force to be adjusted within a range from F1 to F2.

As described above, according to the manipulator 1 of the present embodiment, since the first buffer parts 15B and 16B are formed, since the first spring constants being set appropriately, when the pulling amount of the manipulation member 20 falls within the first range it is possible to grasp the object with a grasping force equal to or smaller than F1 that does not damage to the object. Since the stoppers 17A and 18A are formed, the buffering action of the first buffer parts 15B and 16B can be cancelled by performing manipulation so as to have a pulling amount greater than the first range, and the object can be grasped with a greater grasping force.

Accordingly, for example, when grasping biological tissue susceptible to damage, or when easily grasping a surgical instrument such as a curved needle to adjust a direction of the leading end, it is possible to grasp the biological tissue or the surgical instrument with a relatively small grasping force without separation and in a stable way. Further, when a comparatively great grasping force is required, as when piercing the tissue with the curved needle, it is possible to reliably grasp the curved needle with a relatively great grasping force, and then to conduct a procedure. As a result, the manipulator capable of selectively using the state where it is possible to easily grasp the object with a relatively small grasping force and the state where it is possible to generate a greater and adjustable grasping force, according to a kind of the object or manipulation mode is obtained.

Further, in the manipulator 1 of the present embodiment, the second buffer parts 15C and 16C having a greater spring constant than the first buffer parts 15B and 16B are provided. As such, when the pulling amount is within the second range, the pulling amount of the manipulation member 20 is adjusted, and thus it is possible to grasp the object while a grasping force greater than the grasping force held by the first buffer parts is adjusted within the range from F1 to F2. Thus, it is possible to stably grasp the object with two different magnitudes of grasping force, and to conduct a procedure more preferably.

Further, the lengths of the stoppers 17A and 18A vary, so that it is possible to adjust a timing when the buffering action of the first buffer parts is cancelled. Thus, it is possible to preferably adjust a length of the aforementioned first range according to a kind of the object or a content of the procedure or the like.

In the present embodiment, the example where both of the first forceps piece 11 and the second forceps piece 12 are provided with the first buffer parts has been described. However, the first buffer part or the stopper or the like may be formed on only one of the pair of forceps pieces.

Next, a second embodiment of the present invention will be described with reference to FIG. 5. A manipulator 41 of the present embodiment is different from the manipulator 1 of the first embodiment in that a gripping part has a different structure. Further, in the following description, the same reference numbers are used to designate components similar or equivalent to the members that have already been described, and so repetitive description thereof will be omitted.

Figure 5:
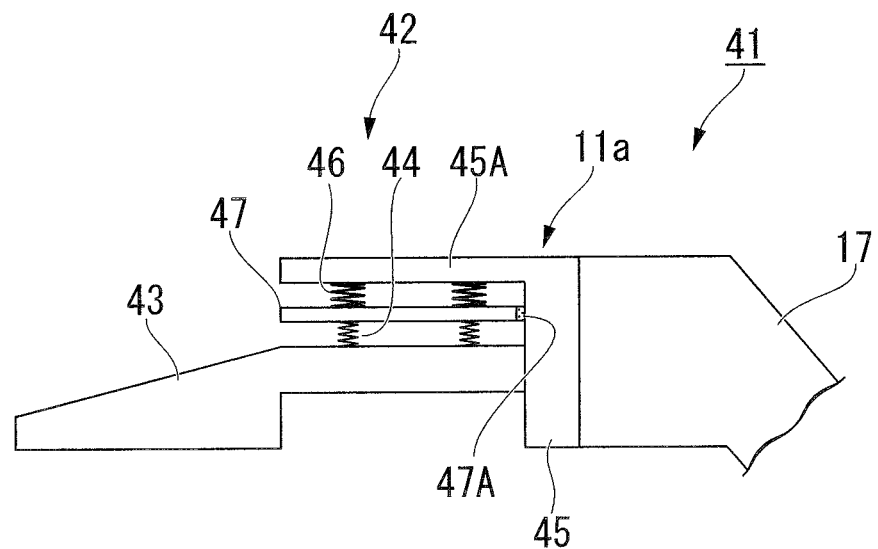
FIG. 5 is a partially enlarged view showing a first forceps piece of a manipulator according to a second embodiment of the present invention.

FIG. 5 is a partially enlarged view showing a first forceps piece 11a of the manipulator 41. A gripping part 42 includes a gripping member 43 attached to a leading end side of a main body 17, a first spring (a buffer part) 44 connected to the gripping member 43, a base body 45 having a first stopper 45A which is rigid and regulates movement of the gripping member 43, a second spring (a second buffer part) 46 connected to the first stopper, and a second stopper (a stopper) 47 disposed between the first spring 44 and the second spring 46.

The gripping member 43 is provided with no elastically deformed part, and has rigidity in whole. A base end side of the gripping member 43 is inserted into a groove (not shown) formed in the base body 45. Thereby, the gripping member 43 is allowed to slide along the groove in parallel to a plane on a leading end side of the base body 45.

The first spring 44 is connected to the gripping member 43 at one end thereof, and is connected to the second stopper 47 at the other end thereof. The second spring 46 is connected to the second stopper 47 at one end thereof, and is connected to the first stopper 45A at the other end thereof. A spring constant of the second spring 46 is larger than that of the first spring 44.

Further, in FIG. 5, the first spring 44 and the second spring 46 are disposed as two. However, the number of springs may be approximately set.

The second stopper 47 is disposed so as to be sandwiched between the first spring 44 and the second spring 46. A base end side of the second stopper 47 which is in contact with the base body 45 is provided with a lock part 47A having a high frictional coefficient. A structure of the lock part 47A is not substantially restricted. For example, the lock part 47A may be formed by surface roughening such as plasma processing. Further, the lock part 47A may be formed by attaching a member having a high frictional coefficient such as rubber or the like.

The second stopper 47 is configured so as not to move relative to the base body 45 until the first spring 44 is compressed to undergo a predetermined amount of elastic deformation by a frictional force generated between the lock part 47A and the base body 45. When the first spring undergoes the elastic deformation at an amount exceeding the predetermined amount, the second stopper slides relative to the base body 45, and regulates the first spring so as not to undergo additional elastic deformation.

Further, only the first forceps piece 11a is shown in FIG. 5, but a second forceps piece is also configured in a similar way.

Operation of the manipulator 41 configured as described above when in use will be described.

When the gripping part 42 grasps an object S, the gripping member 43 slides toward the second stopper 47. The first spring 44 is compressed, and a grasping force increases on the basis of the spring constant of the first spring 44 and the pulling amount of the manipulation member 20. At this time, the second stopper 47 is held without movement by a frictional force generated from the lock part 47A. As such, the second spring 46 is not yet compressed.

When the first spring 44 is elastically deformed beyond a predetermined amount, and when the pulling amount of the manipulation member 20 increases, the gripping member 43, the first spring 44, and the second stopper 47 move so as to approach the first stopper 45A. Therefore, the second spring 46 is compressed, and the grasping force increases on the basis of the spring constant of the second spring 46 and the pulling amount of the manipulation member 20.

After the second spring 46 is fully compressed, the sliding of the gripping member 43 is regulated by the first stopper 45. As such, no buffering action is generated by the first spring 44 and the second spring 46. Here, if the pulling amount does not reach an upper limit, the pulling amount further increases, and thus the grasping force increases sharply. Within the range of the pulling amount up to the upper limit, whether or not to set the sharply increasing range of the grasping force depends on, for instance, setting of the spring constants of the first spring 44 and the second spring 46.

As in the manipulator 1 according to the first embodiment, the manipulator 41 of the present embodiment can selectively use the state where it is possible to easily grasp the object with a relatively small grasping force and the state where it is possible to generate a greater and adjustable grasping force.

Further, the manipulator 41 of the present embodiment has the first stopper 45A that regulates the sliding of the gripping member 43. As such, after the second spring 46 is fully compressed and thus the buffering action caused by the second spring is lost, the pulling amount of the manipulation member 20 increases within a pullable range, and thus a higher grasping force is generated at the gripping part 42.

Next, a third embodiment of the present invention will be described with reference to FIGS. 6 and 7. A manipulator 51 of the present embodiment is different from that of each of the aforementioned embodiments in that a stopper regulating elastic deformation of a first buffer part is not formed.

Figure 6:
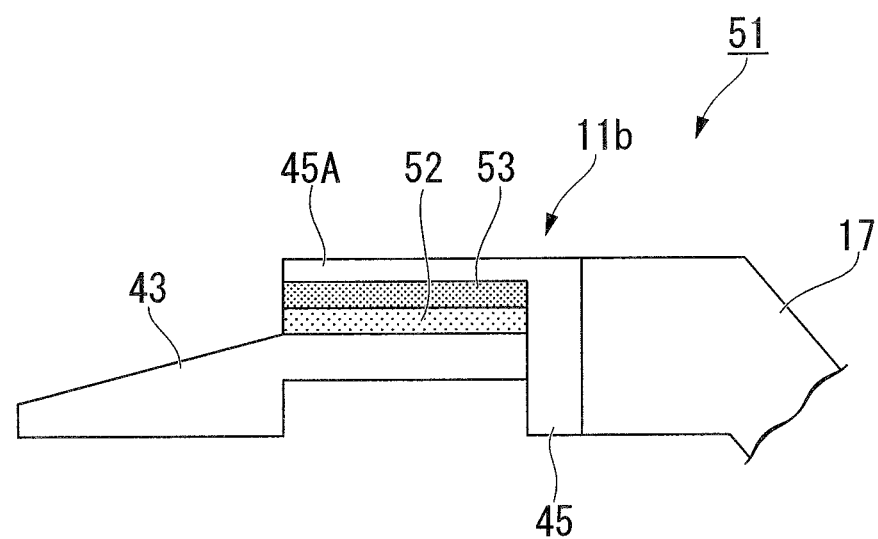
FIG. 6 is a partially enlarged view showing a first forceps piece of a manipulator according to a third embodiment of the present invention.

FIG. 6 is a partially enlarged view showing a first forceps piece 11b of the manipulator 51. A first rubber part (a first buffer part) 52 and a second rubber part (a second buffer part) 53 are disposed between a gripping member 43 and a first stopper 45A. A spring constant of the second rubber part 53 located on the side of the first stopper 45A is greater than that of the first rubber part 52.

Unlike the first embodiment and the second embodiment, the manipulator 51 is configured so that no stopper is installed between the first rubber part 52 and the second rubber part 53. Therefore, when the manipulator 51 is used, the compression of the first rubber part 52 is not stopped halfway. Accordingly, during the compression of the first rubber part 52, the second rubber part 53 is compressed little by little.

Figure 7:
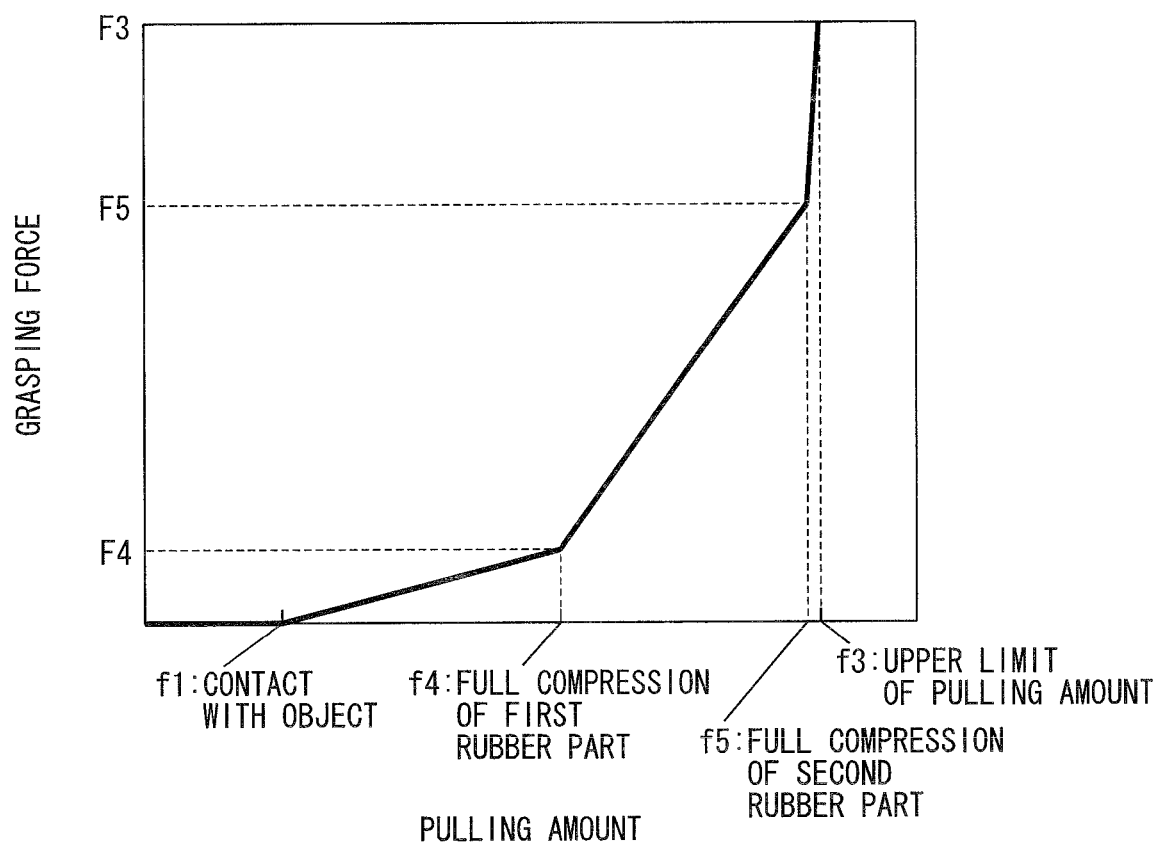
FIG. 7 is a graph schematically showing a relationship between a pulling amount and a grasping force in the manipulator.

FIG. 7 is a graph schematically showing a relationship between a pulling amount and a grasping force in the manipulator 51. As shown in FIG. 7, until the pulling amount becomes f4 which is a magnitude when the first rubber part 52 is compressed up to the limit (i.e. is fully compressed), the grasping force increases on the basis of a resultant spring constant which is a sum of a spring constant of the first rubber part 52 and a spring constant of the second rubber part 53, and the pulling amount of the manipulation member 20. After the first rubber part 52 is fully compressed, only the second rubber part 53 is compressed to undergo elastic deformation. For this reason, the grasping force increases on the basis of the spring constant of the second rubber part 53 and the pulling amount of the manipulation member 20. When the magnitude of the pulling amount becomes f5, and when the second rubber part 53 is compressed up to the limit, no buffering action occurs. Thereafter, when the pulling amount increases, the grasping force increases sharply until the pulling amount becomes an upper limit of f3. At this time, the grasping force becomes an upper limit value F3

Like the manipulators of the first and second embodiments, the manipulator 51 of the present embodiment can selectively use the state where it is possible to easily grasp the object with a relatively small grasping force and the state where it is possible to generate a greater and adjustable grasping force.

Further, since the stopper regulating the elastic deformation of the first rubber part 52 is not provided, a manipulator having a simpler configuration is obtained.

Next, a fourth embodiment of the present invention will be described with reference to FIGS. 8 to 10. A manipulator 61 of the present embodiment is different from that of each of the aforementioned embodiments in that arrangement positions of first and second buffer parts or the like are different.

Figure 8:
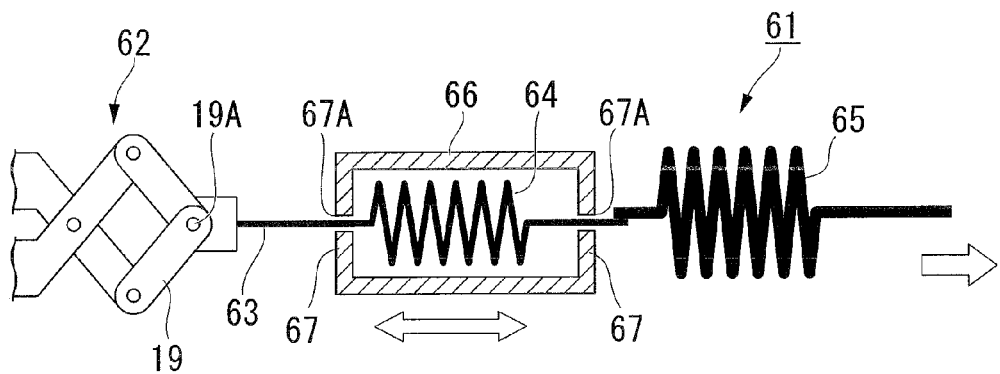
FIG. 8 shows a part of the manipulator according to the third embodiment of the present invention.

FIG. 8 is a schematic view partially showing a treatment part 62 and a manipulation member 63 in the manipulator 61. The manipulation member 63 includes a first spring part (a buffer part) 64 which have a coil shape and a second spring part (a second buffer part) 65 which have a coil shape in part. The first spring part 64 and the second spring part 65 can be expanded or contracted in an axial direction of the manipulation member 63. A wire which forms the second spring part 65 is thicker than that of which forms the first spring part 64, and the second spring part 65 has a greater spring constant than the first spring part 64.

A stopper 66 is mounted around the first spring part 64. The stopper 66 is formed in a cylindrical shape, and is provided with a wall part 67 having a through-hole 67A at either end thereof in an axial direction. Since the stopper 66 is formed of a rigid material, the first spring part 64 is not expanded beyond the length in the axial direction of the stopper 66.

In the manipulator 61 of the present embodiment, when a pulling amount of the manipulation member 63 falls within a first range, the first spring part 64 expands in the axial direction of the manipulation member 63. As a result, due to a buffering action of the first spring part 64, a grasping force increases mainly based on the spring constant of the first spring part 64 and the pulling amount of the manipulation member 63.

Figure 9:
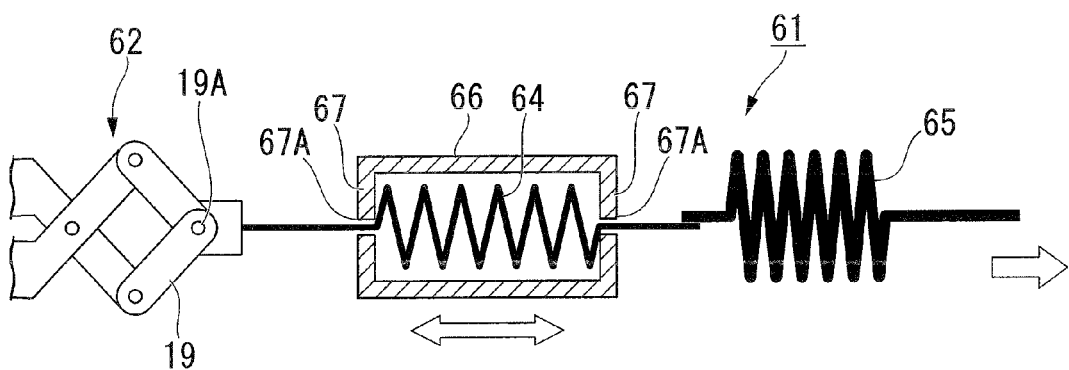
FIG. 9 shows operation when the manipulator is in use.

As shown in FIG. 9, when the both ends of the first spring part 64 come into contact with the wall parts 67 of the stopper 66, the elastic deformation of the first spring part 64 is regulated by the stopper 66, and thus is no longer expanded. Therefore, the buffering action of the first spring part 64 is cancelled.

Figure 10:
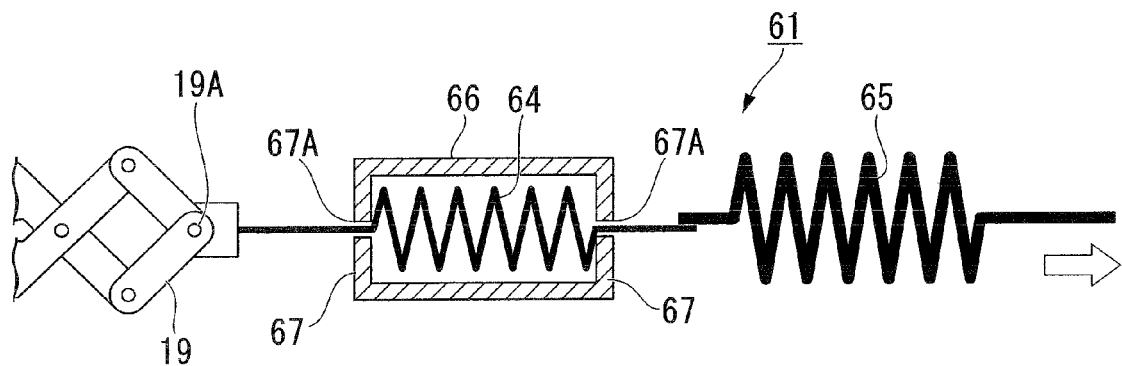
FIG. 10 shows operation when the manipulator is in use.

Afterwards, when the pulling amount falls within a second range, as shown in FIG. 10, only the second spring part 65 begins to be expanded, and the grasping force increases based on the spring constant of the second spring part 65 and the pulling amount of the manipulation member 63 due to a buffering action of the second spring part 65.

Like the manipulators of the other embodiments, the manipulator 61 of the present embodiment can selectively use the state where it is possible to easily grasp the object with a relatively small enough grasping force to not cause damage to the object and the state where it is possible to generate a greater and adjustable grasping force.

Further, in the manipulator 61 of the present embodiment, the first spring part 64, the second spring part 65, and the stopper 66 are installed on the manipulation member 63. Therefore, in the manipulator 61 of the present embodiment, the treatment part 62 can be miniaturized. Thus, a structure of the present embodiment is suitable for a manipulator used, especially, on a narrow region.

Next, a fifth embodiment of the present invention will be described with reference to FIGS. 11A to 11C. A manipulator of the present embodiment is different from that of each of the aforementioned embodiments in that a stopper regulating elastic deformation of a first buffer part and a stopper regulating elastic deformation of a second buffer part are formed on a forceps piece.

Figure 11A:
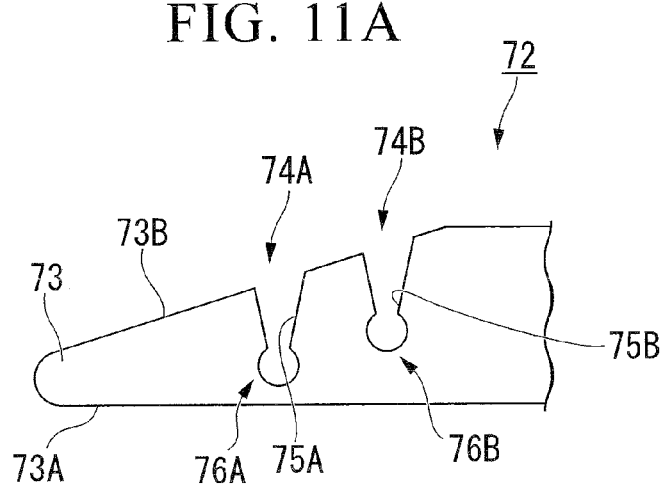
FIG. 11A is a partially enlarged view showing a first forceps piece of a manipulator according to a fifth embodiment of the present invention.
Figure 11B:
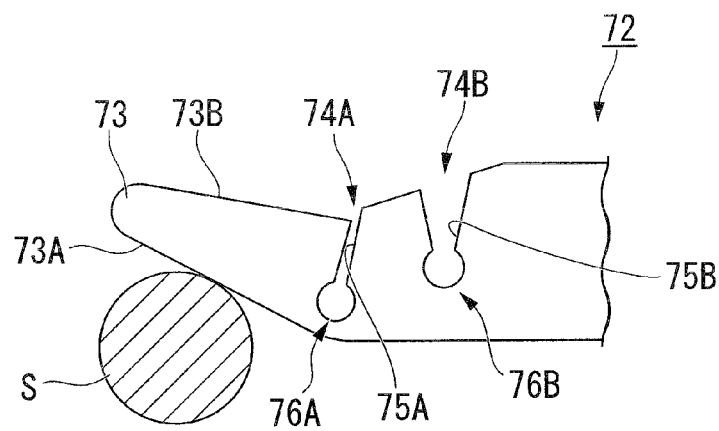
FIG. 11B shows operation when the manipulator is in use.
Figure 11C:
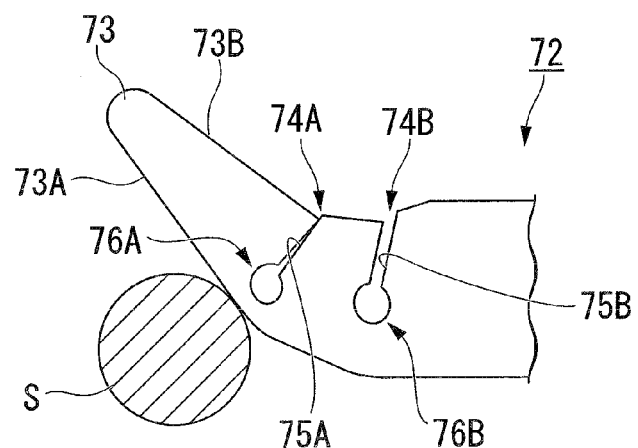
FIG. 11C shows operation when the manipulator is in use.

FIG. 11A is a partially enlarged view showing a gripping member 73 of a gripping part 72 of the manipulator according to the embodiment. The gripping member 73 includes a first spring part 74A formed in a lateral face 73B on an opposite side of a grasping face 73A, and a second spring part 74B formed on a base end side from the first spring part 74A.

A first stopper 75A and a second stopper 75B are slit-shaped groove portions formed from the lateral face 73B on an opposite side of the grasping face 73A toward the grasping face 73A in the gripping member 73. The groove portions forming the first stopper 75A and the second stopper 75B gradually become narrow toward the grasping face 73A, and bottoms of the groove portions are formed in a cylindrical shape parallel to pivoting axes (not shown) of a treatment part.

In the gripping member 73, portions located between the bottoms and the grasping face 73A function as a first buffer part 76A and a second buffer part 76B, respectively. Further, in terms of the opening/closing direction of the treatment part, the second buffer part 76B is formed thicker than the first buffer part 76A. As a result, a spring constant of the second buffer part 76B (a second spring constant) is greater than a spring constant of the first buffer part 76A (a first spring constant).

Next, operation of the manipulator of the present embodiment which is configured as described above when in use will be described.

When the gripping part 72 grasps an object S, the gripping member 73 is displaced such that the groove of the first stopper becomes narrow (i.e. opposite faces of the first stopper 75A come near each other). Therefore, the first spring part 74A is compressed, and the grasping force increases based on the spring constant of the first spring part 74A. At this time, the second spring part 74B is not yet compressed (FIG. 11B).

When the opposite faces of the first stopper 75A come into contact with each other, the gripping member 73 including the first spring part 74A is displaced such that opposite faces of the second stopper 75B come near each other. Therefore, the second spring part 74B is compressed, and the grasping force increases based on the spring constant of the second spring part (FIG. 11C).

After the opposite faces of the second stopper 75B come into contact with each other, the compression of the gripping member 73 is regulated by the second stopper 75B. As such, no buffering action based on the first spring part 74A and the second spring part 74B occurs.

In the manipulator of the present embodiment, the stopper regulating the elastic deformation of the first buffer part and the stopper regulating the elastic deformation of the second buffer part are formed on the gripping member 73. Therefore, a manipulator having a small number of constituent parts and a simple structure is obtained.

While embodiments of the present invention have been described, the technical scope of the present invention is not limited to the embodiments, and may include any design in the scope without departing from the subject matter of the present invention. For example, the present invention may change a combination of the components of each embodiment, apply a variety of modifications to each component, or eliminate each component.

For example, in each of the aforementioned embodiments, the example where the first buffer part and the second buffer part are provided has been described. However, as long as at least the first buffer part and the stopper are provided, the first range and the second range may be set as the pulling amounts. Accordingly, the manipulator of the present invention may be configured so as not to have the second buffer part.

Further, three or more buffer parts may be provided. In this case, stable grasping may be performed with a grasping force further divided in multiple steps.

According to the manipulator of the present invention, it is possible to selectively use the state where it is possible to easily grasp the object with a relatively small grasping force and the state where it is possible to generate a greater and adjustable grasping force.

The invention claimed is:

1. A manipulator comprising:
   a first forceps piece comprising a first gripping surface, and
   a second forceps piece comprising a second gripping surface,
   wherein the first forceps piece and the second forceps piece together form a pair of forceps pieces, and
   wherein the first forceps piece and the second forceps piece are coupled to an axle so as to be pivotable in relation to each other to exert a grasping force through the first gripping surface and the second gripping surface on an object arranged between the first forceps piece and the second forceps piece; and
   a manipulation member operatively connected to a base end side of the pair of forceps pieces, the manipulation member being configured to be operated to pivot the pair of forceps pieces about the axle to grasp the object;
   wherein at least one of the first forceps piece and the second forceps piece further comprises:
      a first buffer part having a first spring constant, wherein the first buffer part is configured to be elastically deformed in accordance with the first spring constant and an operation amount of the manipulation member to change the grasping force acting on the object;
      a second buffer part having a second spring constant that is greater than the first spring constant, wherein the second buffer part is configured to be elastically deformed in accordance with the second spring constant and the operation amount of the manipulation member to change the grasping force acting on the object; and
      a stopper configured to come into contact with the second buffer part to regulate an elastic deformation of the first buffer part and to permit an elastic deformation of the second buffer part upon regulation of the elastic deformation of the first buffer part.

2. The manipulator according to claim 1, wherein the stopper is configured to allow change of a timing when the elastic deformation of the first buffer part is regulated.

3. The manipulator according to claim 1, further comprising:
   a link mechanism comprising a joint,
   wherein the link mechanism operatively connects the manipulation member to the base end side of the pair of forceps pieces, and the joint of the link mechanism is configured to move toward or away from the axle based on the operation of the manipulation member to pivot the pair of forceps pieces about the axle.

4. The manipulator according to claim 1, further comprising a slider slidably mounted on a base end side of the manipulation member.

5. The manipulator according to claim 1, wherein the stopper is formed of a rigid material having no flexibility.

* * * * *